(12) United States Patent
Ohashi et al.

(10) Patent No.: US 6,689,173 B2
(45) Date of Patent: Feb. 10, 2004

(54) HAIR DYE COMPOSITION

(75) Inventors: Yukihiro Ohashi, Sumida-ku (JP);
Hajime Miyabe, Sumida-ku (JP);
Kenichi Matsunaga, Sumida-ku (JP);
Shintaro Totoki, Sumida-ku (JP);
Yoshinori Saito, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/891,202

(22) Filed: Jun. 26, 2001

(65) Prior Publication Data

US 2002/0020030 A1 Feb. 21, 2002

(30) Foreign Application Priority Data

Jun. 27, 2000 (JP) ......................................... 2000-193179

(51) Int. Cl.[7] ................................................. A61K 7/13
(52) U.S. Cl. ....................... 8/405; 8/406; 8/425; 8/423; 8/451; 8/455; 8/454
(58) Field of Search ............................ 8/405, 406, 425, 8/423, 455, 451, 454

(56) References Cited

U.S. PATENT DOCUMENTS

| 5,733,343 A | 3/1998 | Möckli | 8/426 |
| 5,879,412 A | 3/1999 | Rondeau et al. | 8/411 |
| 5,888,252 A | 3/1999 | Möckli | 8/426 |
| 5,980,587 A | 11/1999 | Samain | 8/426 |
| 5,993,490 A * | 11/1999 | Rondeau et al. | 8/409 |
| 6,001,135 A * | 12/1999 | Rondeau et al. | 8/407 |

FOREIGN PATENT DOCUMENTS

| DE | 35 31 773 | 3/1987 | |
| DE | 35 31 774 | 3/1987 | |
| DE | 3531774 A1 * | 3/1987 | ........... C09B/17/02 |
| DE | 197 46 137 | 4/1999 | |
| JP | 6-271435 | 9/1994 | |
| JP | 8-501322 | 2/1996 | |
| JP | 8-507545 | 8/1996 | |
| JP | 10-502946 | 3/1998 | |
| JP | 10-194942 | 7/1998 | |
| WO | WO 95/15144 | 6/1995 | |

* cited by examiner

*Primary Examiner*—Yogendra N. Gupta
*Assistant Examiner*—Eisa Elhilo
(74) *Attorney, Agent, or Firm*—Oblon, Spivak, McClelland, Maier & Neustadt, P.C.

(57) ABSTRACT

Provided is a hair dye composition containing a direct dye (1). This hair dye composition has markedly high hair dyeing power, has less color fade over time and undergoes a small change in the color tone of the dye even after storage.

(1)

wherein, $R^1$ to $R^4$ each represents a (substituted) $C_{1-6}$ alkyl group, (substituted) alkenyl group or (substituted) aryl group or $R^3$ and $R^4$, when taken together with the adjacent C, form a 5 to 12 membered ring, $R^5$ represents H, (substituted) $C_{1-6}$ alkyl group, (substituted) alkenyl group, (substituted) aryl group or acyl group, $X^1$ and $X^2$ each represents H or halogen atom, $Y^1$ and $Y^2$ each represents H, (substituted) $C_{1-6}$ alkyl group, (substituted) alkenyl group, (substituted) $C_{1-6}$ alkoxy group or halogen atom, $Z^1$ and $Z^2$ each represents H, (substituted) $C_{1-6}$ alkyl group, (substituted) alkenyl group, (substituted) $C_{1-6}$ alkoxy group, nitro group or halogen atom, and $A^-$ represents an anion.

24 Claims, No Drawings

HAIR DYE COMPOSITION

TECHNICAL FIELD

The present invention relates to a hair dye composition having markedly high dyeing power, can strongly impart the hair with an extremely vivid red color, has less color fade over time and undergoes a small change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that when the cationic group is contained in an azo-based (—N=N—) conjugated system, they are unstable to an alkali agent or a reducing agent essentially contained in a permanent hair dye.

DISCLOSURE OF THE INVENTION

An object of the present invention is to provide a hair dye composition which has high hair dyeing power, less color fade over time, and excellent storage stability to permit only a small change in color tone of the dye after storage.

The present inventors have found that when the below-described compound which is known, in Offenlegungsschrift DE-3531774, as a cationic dye for dyeing or printing therewith fiber materials, paper or leather, is used as a hair dye, the resulting hair dye composition can strongly impart the hair with an extremely vivid red color without decomposing the dye upon hair dyeing, exhibits excellent light resistance, washing resistance, perspiration resistance, friction resistance and heat resistance, and undergoes a small change in the color tone of the dye after storage as compared with that rightly after preparation because the dye exists in the composition stably.

In one aspect of the present invention, there is thus provided a hair dye composition comprising, as a direct dye, a compound represented by the following formula (1):

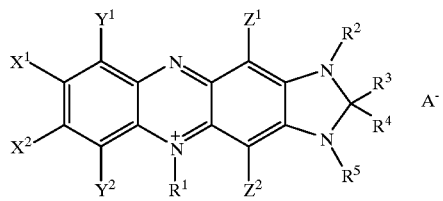

(1)

wherein, $R^1$, $R^2$, $R^3$ and $R^4$ each independently represents a $C_{1-6}$ alkyl group which may have a substituent, an alkenyl group which may have a substituent or an aryl group which may have a substituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $X^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, $Z^1$ and $Z^2$ represents a hydrogen atom, a $C_{1-6}$ alkyl group which may have a substituent, an alkenyl group which may have a substituent, a $C_{1-6}$ alkoxy group which may have a substituent, a nitro group or a halogen atom, and $A^-$ represents an anion.

In another aspect of the present invention, there is also provided a method for dyeing the hair with the above-described hair dye composition.

BEST MODE FOR CARRYING OUT THE INVENTION

In the formula (1), examples of the $C_{1-6}$ alkyl group represented by $R^1$, $R^2$, $R^3$, $R^4$, $R^5$, $Y^1$, $Y^2$, $Z^1$ or $Z^2$ include methyl, ethyl, propyl, isopropyl and cyclohexyl groups, each of which may be substituted by an aryl group, alkoxy group, amino group, mono-or di-($C_{1-4}$ alkyl)-substituted amino group, tri($C_{1-4}$ alkyl)-substituted ammoniumyl group, acyl group, hydroxy group, cyano group or halogen atom.

Examples of the $C_{1-6}$ alkoxy group represented by $Y^1$, $Y^2$, $Z^1$ or $Z^2$ include methoxy, ethoxy, propoxy and isopropoxy and groups, each of which may be substituted by an aryl group, alkoxy group, amino group, mono- or di-($C_{1-4}$ alkyl)-substituted amino group, tri($C_{1-4}$ alkyl)-substituted ammoniumyl group, acyl group, hydroxy group, cyano group or halogen atom.

Examples of the alkenyl group represented by $R^1$, $R^2$, $R^3$, $R^4$, $R^5$, $Y^1$, $Y^2$, $Z^1$ or $Z^2$ include vinyl and allyl groups, each of which may be substituted by an aryl group, an alkoxy group, amino group, mono- or di-($C_{1-4}$ alkyl)-substituted amino group, tri($C_{1-4}$ alkyl)-substituted ammoniumyl group, acyl group, hydroxy group, cyano group or halogen atom.

Examples of the aryl group represented by $R^1$, $R^2$, $R^3$, $R^4$ or $R^5$ include phenyl and naphthyl groups, each of which may be substituted by an alkyl group, aryl group, alkoxy group, amino group, hydroxy group, cyano group, nitro group, trifluoromethyl group or halogen atom, more specifically, methyl group, ethyl group, methoxy group, ethoxy group, chlorine atom or bromine atom.

Examples of the 5- to 12-membered ring formed by $R^3$ and $R^4$ when they are taken together with the adjacent carbon atom include cyclopentane and cyclohexane rings.

Examples of the anion represented by A⁻ in the formula (1) include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions.

Specific examples of the direct dye (1) to be used in the present invention.

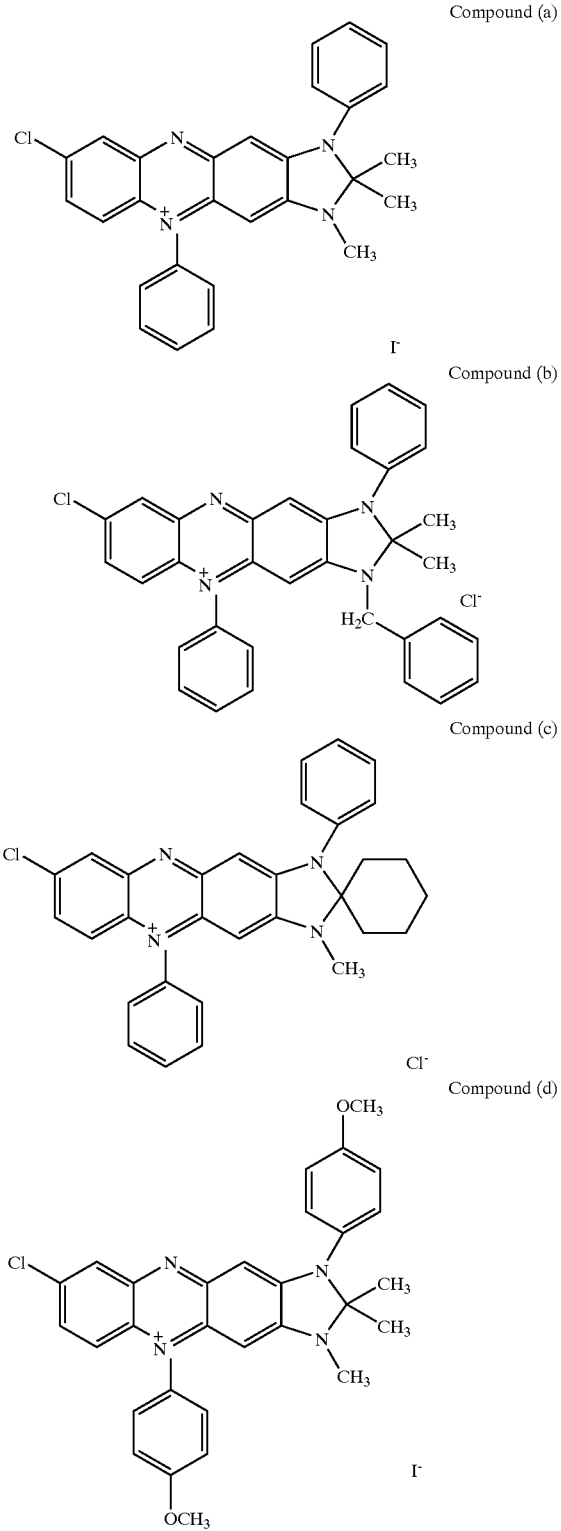

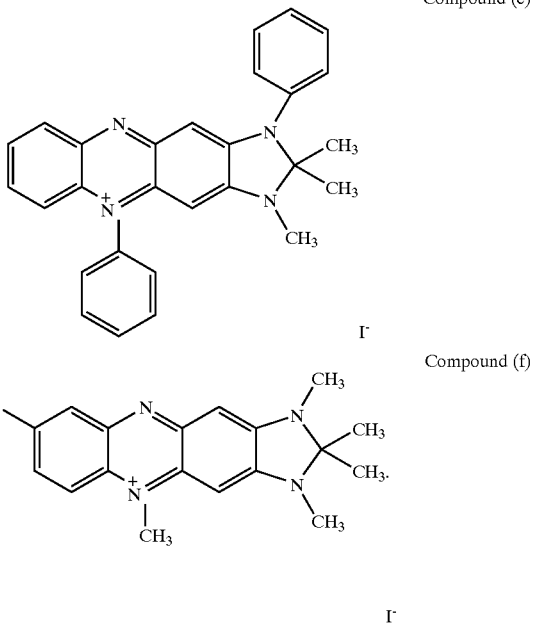

As a direct dye, at least one of these direct dyes (1) can be used or another direct dye can be used in combination therewith. In particular, combination with yellow and blue dyes makes it possible to dye the hair with a deep and highly lustrous dark brown or black color.

Examples of the direct dye other than the direct dyes (1) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57 (C.I. 12719); and basic dyes as described in Japanese Patent Publication No. Sho 58-2204, Japanese Patent Application Laid-Open No. Hei 9-118832, Japanese Language Laid-Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % based on the whole composition (after mixture of all the component parts when the hair dye composition is a two part or three part type; this will apply equally hereinafter). When another direct dye is added in combination, the content of it in total with the direct dye (1) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. In this case, the above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from groups $NH_2$-, NHR- and $NR_2$- (in which R represents a $C_{1-4}$ alkyl group or a hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives, p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As each of a developer and a coupler, at least one of the above-exemplified ones can be used. Although no particular limitation is imposed on the content of each of them, it is added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of the anionic component/ion activity concentration of the cationic direct dye (1)≦8"

The term "ion activity concentration" as used herein means "molar concentration ×ionic valence".

Addition of a polyol, polyol alkyl ether, cationic or amphoteric polymer or silicone to the hair dye composition of the present invention is preferred, because the resulting composition can dye the hair uniformly and has improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (1) can be incorporated in either one or both of these component parts of the two-part or three-part composition. When the hair dye composition of the present invention is one-part type, it is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the components when the hair dye composition is a two-part or three-part type).

EXAMPLES

Examples 1 to 5

In a manner known per se in the art, hair dyes as shown in Table 1 were prepared.

TABLE 1

| (wt. %) | Examples | | | | |
| --- | --- | --- | --- | --- | --- |
|  | 1 | 2 | 3 | 4 | 5 |
| Dye [Compound (d)] | 0.2 |  | 0.15 | 0.1 |  |
| Dye [Compound (a)] |  | 0.5 |  | 0.1 | 0.2 |
| Dye [formula (I), Red] |  |  | 0.15 |  |  |
| Dye [formula (II), Yellow] |  |  | 0.1 | 0.1 | 0.05 |
| Ethanol |  | 5 |  | 5 | 5 |
| Propylene glycol |  |  | 5 |  | 5 |
| Diethylene glycol monoethyl ether |  | 10 |  |  |  |
| Guar gum | 1 |  |  |  |  |
| Hydroxypropyl guar gum |  | 1 | 1 | 1 | 1 |
| "Gufquat 734" (trade name; product of ISP Japan) | 1 |  | 1 |  |  |
| "Catinal LC100" (trade name; product of Toho Chemical Industry) |  | 1 |  |  | 1 |
| "Polyether-modified silicone KF6005" (trade name; product of Shin-Etsu Chemical) |  |  |  |  | 0.4 |
| "Amodimethicone SM8702C" (trade name; product of Dow Corning Toray Silicone) |  |  |  | 1.5 |  |
| Monoethanolamine | 0.1 | | | | |
| Phosphoric acid | Amount to adjust pH to 9 | | | | |
| Perfume | q.s. | | | | |
| Water | Balance | | | | |

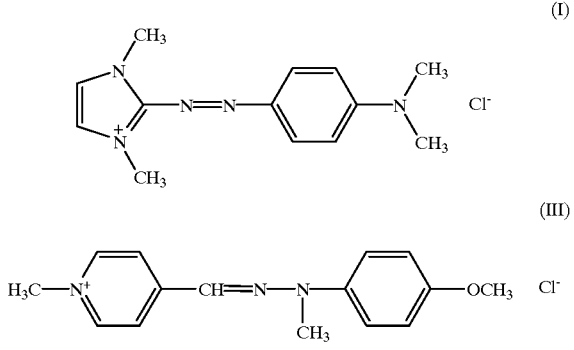

Examples 6 to 9

In a manner known per se in the art, hair dyes as shown in Table 2 were prepared.

TABLE 2

| (wt. %) | Examples | | | |
|---|---|---|---|---|
| | 6 | 7 | 8 | 9 |
| 1st part | | | | |
| Dye [Compound (b)] | 0.2 | | 0.15 | 0.2 |
| Dye [Compound (c)] | | 0.1 | 0.15 | |
| Dye [formula (II), Yellow] | | 0.1 | | 0.05 |
| Dye [Basic Blue 99] | | 0.3 | | |
| 28 wt. % Aqueous ammonia | 5 | | | |
| Monoethanolamine | 2 | | | |
| Propylene glycol | 8 | | | |
| Polyoxyethylene (20) isostearyl ether | 24 | | | |
| Polyoxyethylene (2) isostearyl ether | 20 | | | |
| "Merquat 280" (trade name; product of Calgon Corp., a 35 wt. % aqueous solution) | 8 | | | |
| "Polymer JR400" (trade name; product of Union Carbide) | | 0.5 | | 0.5 |
| "Amodimethicone SM8702C" (trade name; product of Dow Corning Toray Silicone) | | | 2 | |
| "Polyether modified silicone KF6005" (trade name; product of Shin-Etsu Chemical) | | | | 0.3 |
| Tetrasodium ethylenediaminetetraacetate | 0.1 | | | |
| Perfume | q.s. | | | |
| Ammonium chloride | Amount to adjust pH to 10 | | | |
| Water | Balance | | | |
| 2nd part | | | | |
| 35 wt. % Aqueous hydrogen peroxide | 17.1 | | | |
| Methylparaben | 0.1 | | | |
| Phosphoric acid | Amount to adjust pH to 3.5 | | | |
| Water | Balance | | | |

Examples 10 to 12

In a manner known per se in the art, hair dyes as shown in Table 3 were prepared.

TABLE 3

| (wt. %) | Examples | | |
|---|---|---|---|
| | 10 | 11 | 12 |
| 1st part | | | |
| Toluene-2,5-diamine | 1.9 | 1 | |
| Para-aminophenol | | | 1 |
| Resorcin | 2 | | |
| Para-amino-ortho-cresol | | | 1.1 |
| 2,4-Diaminophenoxyethanol | | 1.37 | |
| Dye [Compound (d)] | 0.05 | | |
| Dye [Compound (e)] | | 0.15 | |
| Dye [Compound (f)] | | | 0.1 |

TABLE 3-continued

| (wt. %) | Examples | | |
|---|---|---|---|
| | 10 | 11 | 12 |
| 28 wt. % Aqueous ammonia | 5 | | |
| Monoethanolamine | 2 | | |
| Propylene glycol | 8 | | |
| Polyoxyethylene (20) isostearyl ether | 24 | | |
| Polyoxyethylene (2) isostearyl ether | 20 | | |
| "Merquat 280" (trade name; product of Calgon Corp., a 35 wt. % aqueous solution) | 8 | | |
| "Polymer JR400" (trade name; product of Union Carbide) | | 0.5 | |
| "Amodimethicone SM8702C" (trade name; product of Dow Corning Toray Silicone) | | | 2 |
| Sodium sulfite | 0.05 | | |
| Ascorbic acid | 0.5 | | |
| Tetrasodium ethylenediaminetetraacetate | 0.1 | | |
| Perfume | q.s. | | |
| Ammonium chloride | Amount to adjust pH to 10 | | |
| Water | Balance | | |
| 2nd part | | | |
| 35 wt. % Aqueous hydrogen peroxide | 17.1 | | |
| Methylparaben | 0.1 | | |
| Phosphoric acid | Amount to adjust pH to 3.5 | | |
| Water | Balance | | |

Example 13

In a manner known per se in the art, the following hair dye was prepared.

| | (wt. %) |
|---|---|
| (First part) | |
| Para-aminophenol | 1 |
| Para-amino-ortho-cresol | 1.1 |
| Compound (e) | 0.1 |
| 23 wt. % Aqueous ammonia | 5 |
| Monoethanolamine | 2 |
| Cetanol | 3.8 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |
| (Second part) | |
| 35 wt. % Aqueous hydrogen peroxide | 17.1 |
| Methylparaben | 0.1 |
| Phosphoric acid | Amount to adjust pH to 3.5 |
| Water | Balance |

What is claimed is:
1. A hair dye composition comprising, as a direct dye, a compound represented by the following formula (1):

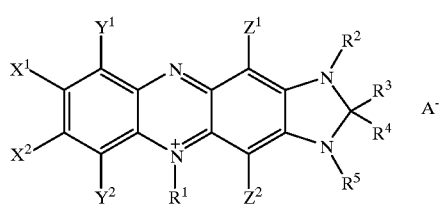

wherein $R^1$, $R^2$, $R^3$ and $R^4$ each independently represents a $C_{1-6}$ alkyl group which may have a substituent, an alkenyl-group which may have a substituent or an aryl group which may have a substituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $Y^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, may have a substitent, an alkenyl group which may have a substituent, a $C_{1-6}$ alkoxy group which may have a substituent or a halogen atom, $Z^1$ and $Z^2$ each independently represents a hydrogen atom, a $C_{1-6}$ alkyl group which may have a substituent, an alkenyl group which may have a substituent, a $C_{1-6}$ alkoxy group which may have a substituent, a nitro group or a halogen atom, and $A^-$ represents an anion the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drugs extracts, vitamins, colorants, perfumes, aerosolizing agents and UV absorbers.

2. A hair dye composition according to claim 1, wherein the compound of formula (1) is selected from the group consisting of the following compounds (a)–(f):

Compound (a)

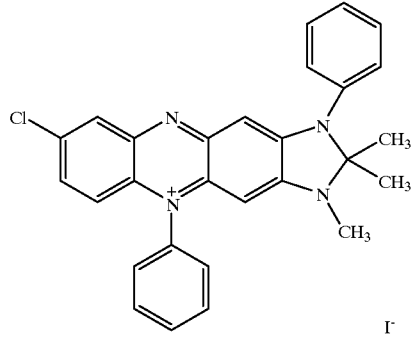

Compound (b)

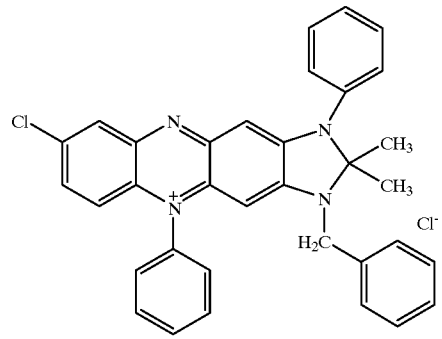

Compound (c)

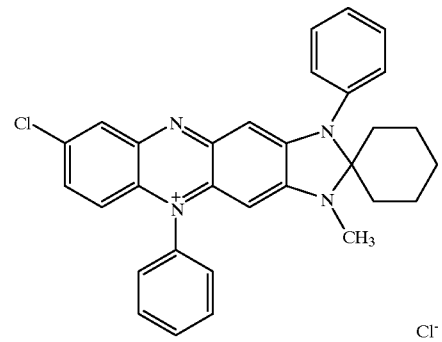

Compound (d)

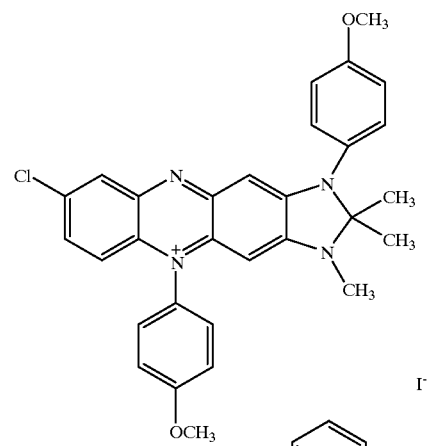

Compound (e)

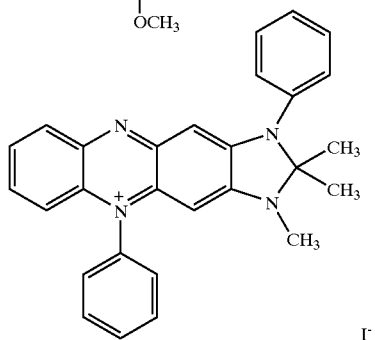

Compound (f)

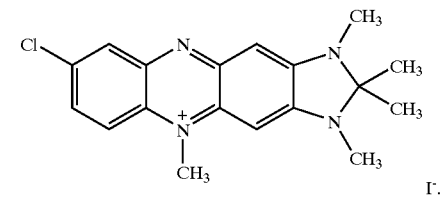

3. The hair dye composition according to claim 1, further comprising one or more direct dyes other than one having said formula (1).

4. The hair dye composition according to claim 1, wherein said compound of formula (1) is present in an amount of 0.01 to 20 wt. % based on the weight of the composition.

5. The hair dye composition according to claim 4, wherein said compound of formula (1) is present in an amount of 0.05 to 10 wt. % based on the weight of the composition.

6. The hair dye composition according to claim 5, wherein said compound of formula (1) is present in an amount of 0.1 to 5 wt. % based on the weight of the composition.

7. The hair dye composition according to claim 3, wherein the total amount of said direct dyes is from 0.05 to 10 wt. %, based on the weight of the composition.

8. The hair dye composition according to claim 7, wherein the total amount of dye is from 0.1 to 5 wt. %, based on the weight of the composition.

9. The hair dye composition according to claim 1, wherein the composition has a pH of 8 to 11.

10. A hair dye composition comprising a two-part aqueous formulation comprising, in a first part, a direct dye compound represented by the following formula (1):

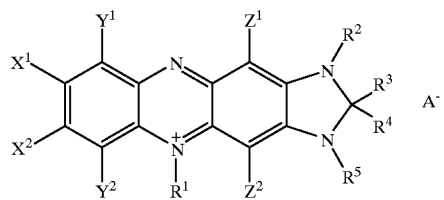

wherein, $R^1$, $R^2$, $R^3$ and $R^4$ each independently represents a $C_{1-6}$ alkyl group which may have a substituent, an alkenyl group which may have a substituent or an aryl group which may have a substituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $X^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, $Z^1$ and $Z^2$ each independently represents a hydrogen atom, a $C_{1-6}$ alkyl group which may have a substituent, an alkenyl group which may have a substituent, a $C_{1-6}$ alkoxy group which may have a substituent, a nitro group or a halogen atom, and $A^-$ represents an anion; the first part having a pH ranging from 6–11 that is adjusted within said range by an alkali agent; and a second part, comprising an aqueous solution of an oxidizing agent.

11. The hair dye composition according to claim 10, wherein the oxidizing agent is hydrogen peroxide, a persulfate, a perborate, a percarbonate or a bromate.

12. The hair dye composition according to claim 10, wherein the oxidizing agent is present in an amount of 0.5 to 10 wt. % based on the weight of the composition.

13. The hair dye composition according to claim 12, wherein the oxidizing agent is present in an amount of 1 to 8 wt. % based on the weight of the composition.

14. The hair dye composition according to claim 12, wherein the oxidizing agent is combined with a color developer and a coupler in the second part of the composition, each of the developer and the coupler being present in an amount of 0.01 to 20 wt. % based on the weight of the composition.

15. The hair dye composition according to claim 10, wherein each of the color developer and a coupler is present in an amount of 0.5 to 10 wt. % based on the weight of the composition.

16. A hair dye composition, comprising:
a three-part aqueous formulation comprising, in a first part, a direct dye compound represented by the following formula (1):

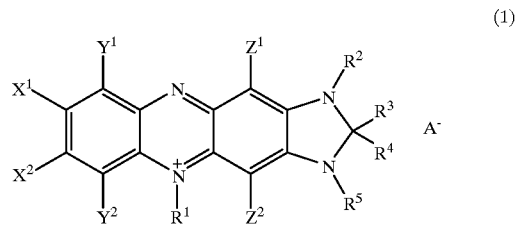

wherein, $R^1$, $R^2$, $R^3$ and $R^4$ each independently represents a $C_{1-6}$ alkyl group which may have a substituent, an alkenyl group which may have a substituent or an aryl group which may have a sub stituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $X^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, $Z^1$ and $Z^2$ each independently represents a hydrogen atom, a $C_{1-6}$ alkyl group which may have a substituent, an alkenyl group which may have a substituent, a $C_{1-6}$ alkoxy group which may have a substituent, a nitro group or a halogen atom, and $X^-$ represents an anion; the first part having a pH ranging from 6–11 that is adjusted within said range by an alkali agent;

a second part, comprising an aqueous solution of an oxidizing agent; and a third part, comprising a powdered oxidizing agent.

17. The hair dye composition according to claim 16, wherein the oxidizing agent of the second part is hydrogen peroxide, a persulfate, a perborate, a percarbonate or a bromate.

18. The hair dye composition according to claim 16, wherein the oxidizing agent of the second part is present in an amount of 0.5 to 10 wt. % based on the weight of the composition.

19. The hair dye composition according to claim 16, wherein the oxidizing agent is combined with a color developer and a coupler in the second part of the composition, each of the developer and the coupler being present in an amount of 0.01 to 20 wt. % based on the weight of the composition.

20. The hair dye composition according to claim 19, wherein each of the color developer and a coupler is present in an amount of 0.5 to 10 wt. % based on the weight of the composition.

21. The hair dye composition according to claim 16, wherein the third part of the composition contains a powdered persulfate oxidizing agent.

22. A method of dyeing hair, comprising:

treating the hair with a one part aqueous formulation containing a direct dye compound represented by the following formula (1):

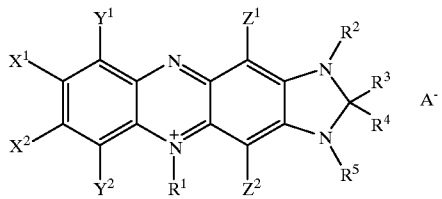

(1)

wherein, $R^1$, $R^2$, $R^3$ and $R^4$ each independently represents a $C_{1-6}$ alkyl group which may have a substituent, an alkenyl group which may have a substituent or an aryl group which may have a substituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $X^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, $Z^1$ and $Z^2$ each independently represents a hydrogen atom, a $C_{1-6}$ alkyl group which may have a substituent, an alkenyl group which may have a substituent, a $C_{1-6}$ alkoxy group which may have a substituent, a nitro group or a halogen atom, and $A^-$ represents an anion, the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drugs extracts, vitamins, colorants, perfumes, aerosolizing agents and UV absorbers.

23. A method of dyeing hair, comprising:

treating the hair with a two-part aqueous formulation comprising, in a first part, a direct dye compound represented by the following formula (1):

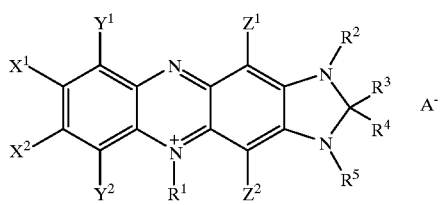

(1)

wherein, $R^1$, $R^2$, $R^2$ and $R^4$ each independently represents a $C_{1-6}$ alkyl group which may have a substituent, an alkenyl group which may have a substituent or an aryl group which may have a substituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $X^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, $Z^1$ and $Z^2$ each independently represents a hydrogen atom, a $C_{1-6}$ alkyl group which may have a substituent, an alkenyl group which may have a substituent, a $C^{1-6}$ alkoxy group which may have a substituent, a nitro group or a halogen atom, and $A^-$ represents an anion, the composition having a pH ranging from 6–11 that is adjusted to within said range by an alkali agent; and a second part, comprising an aqueous solution of an oxidizing agent.

24. A method of dyeing hair, comprising:

treating the hair with a three-part aqueous formulation comprising, in a first part, a direct dye compound represented by the following formula (1):

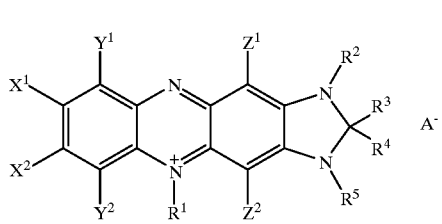

(1)

wherein, $R^1$, $R^2$, $R^2$ and $R^4$ each independently represents a $C_{1-6}$ alkyl group which may have a substituent, an alkenyl group which may have a substituent or an aryl group which may have a substituent, or $R^3$ and $R^4$, when taken together with the adjacent carbon atom, form a 5- to 12-membered ring, $R^5$ represents a hydrogen atom, a $C_{1-6}$ alkyl group which may have a substituent, an alkenyl group which may have a substituent, an aryl group which may have a substituent, or an acyl group, $X^1$ and $X^2$ each independently represents a hydrogen atom or a halogen atom, $Y^1$ and $Y^2$ each independently represents a hydrogen atom, a $C_{1-6}$ alkyl group which may have a substituent, an alkenyl group which may have a substituent, a $C_{1-6}$ alkoxy group which may have a substituent or a halogen atom, $Z^1$ and $Z^2$ each independently represents a hydrogen atom, a $C_{1-6}$ alkyl group which may have a substituent, an alkenyl group which may have a substituent, a $C_{1-6}$ alkoxy group which may have a substituent, a nitro group or a halogen atom, and $A^-$ represents an anion, the first part having a pH ranging from 6–11 that is adjusted to within said range by an alkali agent;

a second part, comprising an aqueous solution of an oxidizing agent; and a third part, comprising a powdered oxidizing agent.

* * * * *

UNITED STATES PATENT AND TRADEMARK OFFICE
CERTIFICATE OF CORRECTION

PATENT NO. : 6,689,173 B2
DATED : February 10, 2004
INVENTOR(S) : Yukihiro Ohashi et al.

It is certified that error appears in the above-identified patent and that said Letters Patent is hereby corrected as shown below:

<u>Column 9,</u>
Lines 24-27, "or a halogen atom, may have a subsitent, an alkenyl group which may have a substituent, a $C_{1-6}$ alkoxy group which may have a substituent or a halogen atom, $Z^1$ and $Z^2$" should read -- or a hologen atom, $Z^1$ and $Z^2$ --.
Line 34, "anion the" should read -- anion, the --.

Signed and Sealed this

Tenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,689,173 B2
DATED : February 10, 2004
INVENTOR(S) : Yukihiro Ohashi et al.

It is certified that error appears in the above-identified patent and that said Letters Patent is hereby corrected as shown below:

Column 9,
Lines 24-27, "or a halogen atom, may have a substitent, an alkenyl group which may have a substituent, a $C_{1-6}$ alkoxy group which may have a substituent or a halogen atom, $Z^1$ and $Z^2$" should read -- or a halogen atom, $Z^1$ and $Z^2$ --.
Line 34, "anion the" should read -- anion, the --.

Signed and Sealed this

Nineteenth Day of April, 2005

JON W. DUDAS
*Director of the United States Patent and Trademark Office*